(12) United States Patent
Du et al.

(10) Patent No.: US 8,187,435 B2
(45) Date of Patent: May 29, 2012

(54) REFERENCE ELECTRODE

(75) Inventors: Yi-Chang Du, Keelung (TW); Bang-Hao Wu, Kaohsiung (TW); Li Duan Tsai, Hsinchu (TW); Hsiung Hsiao, Hsinchu (TW)

(73) Assignee: Industrial Technology Research Institute, Hsinchu County (TW)

( * ) Notice: Subject to any disclaimer, the term of this patent is extended or adjusted under 35 U.S.C. 154(b) by 811 days.

(21) Appl. No.: 12/186,511

(22) Filed: Aug. 5, 2008

(65) Prior Publication Data
US 2009/0166198 A1    Jul. 2, 2009

(30) Foreign Application Priority Data
Dec. 28, 2007  (TW) .............................. 96150818 A

(51) Int. Cl.
*G01N 27/26* (2006.01)
(52) U.S. Cl. ......... 204/400; 204/435; 204/414; 204/415
(58) Field of Classification Search .................... None
See application file for complete search history.

(56) References Cited

U.S. PATENT DOCUMENTS

| | | | | |
|---|---|---|---|---|
| 3,582,474 A | * | 6/1971 | Hair et al. .................. | 205/781.5 |
| 3,676,319 A | * | 7/1972 | Kirsten ........................ | 204/435 |
| 5,334,305 A | | 8/1994 | Okada et al. | |
| 5,360,529 A | * | 11/1994 | Edwards et al. ............... | 204/435 |
| 5,472,590 A | * | 12/1995 | Yamashita et al. ............ | 257/253 |
| 6,419,809 B1 | | 7/2002 | Suzuki et al. | |
| 6,964,734 B2 | | 11/2005 | Cha et al. | |
| 2003/0183517 A1 | * | 10/2003 | Ehrismann et al. ........... | 204/296 |
| 2005/0133369 A1 | * | 6/2005 | Sovrano et al. ............... | 204/435 |

OTHER PUBLICATIONS

Walcarius, Zeolite-modified electrodes in electroanalytical chemistry, Anal. Chim. Acta 384 (1999) 1-16.*

* cited by examiner

*Primary Examiner* — Jeffrey T Barton
*Assistant Examiner* — Steven Rosenwald
(74) *Attorney, Agent, or Firm* — Pai Patent & Trademark Law Firm; Chao-Chang David Pai

(57) ABSTRACT

The invention provides a reference electrode including a liquid electrolyte containing water, a water soluble organic compound with molecular size and boiling point are both greater than water, and an ionic salt; a solid crystal of the ionic salt in the liquid electrolyte; a metal/metal salt complex layer in contact with the liquid electrolyte; an leading wire connected to the metal/metal salt complex layer; an insulation case for containing the liquid electrolyte; and a nano-porous junction material embedded in the insulation case for contacting the liquid electrolyte, wherein a pore size of the nano-porous junction material is greater than a cation diameter of the ionic salt but smaller than a molecular length of the water soluble organic compound. The solid crystal of the ionic salt is the sediment of part of the ionic salt because the amount of the ionic salt is more than its solubility in the liquid electrolyte.

8 Claims, 3 Drawing Sheets

REFERENCE ELECTRODE

CROSS REFERENCE TO RELATED APPLICATIONS

This Application claims priority of Taiwan Patent Application No. 096150818, filed on Dec. 28, 2007, the entirety of which is incorporated by reference herein.

BACKGROUND OF THE INVENTION

1. Field of the Invention

The present invention relates to a reference electrode which will give a reference electric potential for a potentiometric system for detecting ionic matters in a solution. Specifically, the said reference electrode has a nano-porous junction material and a liquid electrolyte containing a water soluble organic compound with the molecular size and boiling point both greater than water.

2. Description of the Related Art

The ion-sensitive field effect transistor (ISFET) has many advantages, such as the miniaturization and is widely used to potentiometrically measure the concentration of specific ions in liqueous samples in household health care or environmental monitoring. To obtain the relationship of the electrical potential and the concentration of the detected matters correctly, a reference electrode offering a stable reference electric potential is needed in the ISFET potentiometric system. However, compared with the size of the ISFET, the size of a traditional Ag/AgCl glass reference electrode is bulky and while it is not being used, it must be stored in saturated KCl solution to prevent the evaporation of the aqueous electrolyte in the reference electrode. Moreover, the traditional Ag/AgCl glass reference electrode is easily polluted by the contaminants in the tested solution through the junction material if the tested solution is not properly addressed prior to the measurement, which results in the shift of the reference electric potential and causes deadly deviations. Therefore, the functions and features of the traditional Ag/AgCl reference electrode are not suitable for an ISFET potentiometric system.

Although much effort has been dedicated to solve some problems of the traditional Ag/AgCl glass reference electrode mentioned above, the achievements are limited. For example, in order to reduce the dry of the traditional reference electrode in the low humidity, Okada et al. suggested adding $NH_4NO_3$, LiCl, agar into the saturated solution of KCl to prepare a gelatinous electrolyte of the Ag/AgCl reference electrode (U.S. Pat. No. 5,334,305). Although $NH_4NO_3$ and LiCl both are hydrophilic, the achievement of improving water loss in the reference electrode is limited.

Moreover, to miniaturize the size of the Ag/AgCl reference electrode, a strategy of silicon-based multilayer technology is widely adopted. In this case, a metal layer such as silver is coated on a ceramic or silicon substrate, and then the surface of the silver layer is oxidized to form an Ag/AgCl complex layer by electrochemical approach or a haloid oxidizer such as ferric chloride. Furthermore, a gelatinous electrolyte and a protective polymeric membrane are coated on the substrate in sequence. Finally, the device is sealed except the polymeric membrane. The performance of the protective polymeric membrane is to reduce the fast leaching out of the electrolytic salts in the electrolyte and prolong the life span of the reference electrode. The higher the leaching rate of the salts in the electrolyte, the shorter the lifespan of the described reference electrode. Reversely, if the leaching of the salts in the electrolyte is too slow, the response of the reference electrolyte will spend a lot of time. In practical, this kind of reference electrode usually needs a preconditioning time to get a stable electric potential by dipping the tested solution before measurement. For example, H. J. Lee et al. published a PU membrane which has been added cation and anion salts as a protective membrane (Anal. Chem., 70 (1998) 3377; Sens. Actuators B, 34(2000) 8; Proc. IEEE, 91 (2003) 870). However, this kind of reference electrode needs one hour of preconditioning time and was impractical. Although Ha et al. further modified the PU membrane with hydrophilic polymer and cellulose acetate to increase the permeability between water and the electrolyte, the reference electrode still needs 1.5-3.5 minutes of preconditioning time and the lifespan of the reference electrode is only 20-100 minutes (Analytica Chimica Acta, 549 (2005) 59). Therefore, according to the present technology, a reference electrode with a small size, a long lifespan, stable electric potential, and easy storage, has yet to be obtained.

BRIEF SUMMARY OF THE INVENTION

The invention provides a reference electrode, comprising: a liquid electrolyte containing water, a water soluble organic compound with molecular size and boiling point both greater than water, and an ionic salt; a solid crystal of the ionic salt in the liquid electrolyte; a metal/metal salt complex layer in contact with the liquid electrolyte; an leading wire connected to the metal/metal salt complex layer; an insulation case for containing the liquid electrolyte; and a nano-porous junction material, wherein a pore size of the nano-porous junction material is greater than a cation diameter of the ionic salt but smaller than a molecular length of the water soluble organic compound.

The said solid crystal of the ionic salt is the sediment of part of the ionic salt because the amount of the ionic salt in this invention is more than its solubility in the said liquid electrolyte.

The insulation case has two open ends. The nano-porous junction material is bound to one open end of the insulation case and the leading wire stretches out from the other open end of the insulation case. The gap between the nano-porous junction material and the insulation case is sealed. The other open end of the insulation case is sealed as well. Therefore, the liquid electrolyte, solid crystal of the ionic salt, a metal/metal salt complex layer are sealed in the insulation case.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The invention comprises a liquid electrolyte, a solid crystal of the ionic salt in the liquid electrolyte, a metal/metal salt complex layer, a lead wire, an insulation case and a nano-porous junction material. The relationship of each component of the invention will be expatiated in the following description.

Figure 1:
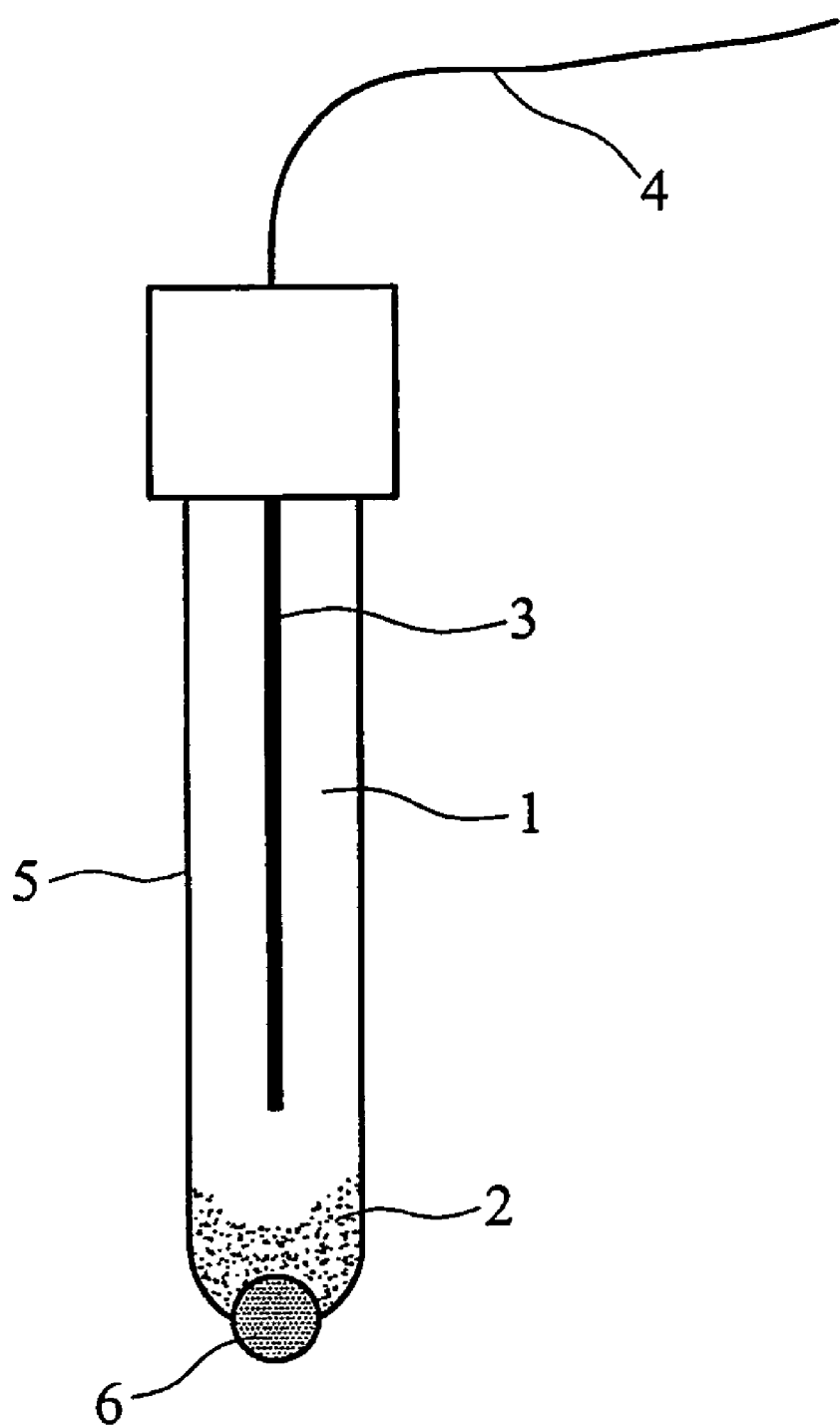
FIG. 1 shows the structure of the reference electrode of one embodiment of the invention.

FIG. 1 shows a reference electrode of one embodiment of the invention. Insulation case 5 contains liquid electrolyte 1 and solid crystal of ionic salt 2. Metal/metal salt complex layer 3 is soaked in liquid electrolyte 1 and is connected to a lead wire 4. Nano-porous junction material 6 is bound to an open end of the insulation case 5 and is in contact with the liquid electrolyte 1.

Liquid electrolyte 1 contains water, a water soluble organic compound with the molecular size and boiling point both greater than water, and an ionic salt. The amount of the ionic salt is more than its solubility in the electrolyte, so part of the ionic salt will not be dissolved in the electrolyte and exits in solid state. In this invention, the solubility of the ionic salt in the selected organic compound is less than in water, thus the mixture of water and the said organic compound has less ability of dissolving the said ionic liquid than pure water. Therefore, the concentration of the dissolved ionic salt in the said mixture is less than in water. Because the diffuse of ions in the liquid depends on its concentration in the solution, the thinner the concentration of the dissolved ions in the solution, the lower the leaching rate of the dissolved ions in the electrolyte of the reference electrode when the reference electrode of the invention is dipped the measured solution, which prolongs the lifespan of the reference electrode. Furthermore, the boiling point of the said organic compound is higher than that of water and the organic compound is hydrophilic so that the mixture of water and the said organic compound in this invention will not be drying out in low humid.

Because of the excess amount of ionic salt added to the liquid electrolyte 1 of the reference electrode, only part of the said ionic salt is dissolved to be ions, and most of the ionic salt remains in the solid crystal of ionic salt 2, thus the solid crystal of ionic salt 2 is the ion "storage" of the liquid electrolyte 1 As the dissolved ions in the electrolyte is gradually leaching out during the reference electrode contacts with the measured solution, the solid of the said ionic salt in the electrode will be therefore continuously dissolved into the electrolyte to maintain a stable ion concentration of the electrolyte for a long period of time.

Note that minimal water content is needed in liquid electrolyte 1 of the invention. In one embodiment, the water content of liquid electrolyte 1 is about 5-50 wt % and preferably less than about 30 wt %. The water soluble organic compound may comprise ethylene glycol, glycerol, poly(ethylene glycol) (PEG), poly(propylene glycol) (PPG), poly(oxyethylene) or hydrophilic poly(siloxane) etc., and preferably poly(ethylene glycol). In one embodiment, the average molecular weight of the poly(ethylene glycol) which is used in the invention is 200. In addition, the vapour pressure of the water soluble organic compounds at operating temperatures are very low, and thus, they do not easily evaporate in low humid and prevent the water in the liquid electrolyte to evaporate. Accordingly, the reference electrode of the invention does not need to be stored in a saturated solution of electrolyte.

Metal/metal salt complex layer 3 mentioned above needs to be in contact with liquid electrolyte 1 and connected to a lead wire 4. Metal/metal salt complex layer 3 may comprise Ag/AgX, Hg/Hg$_2$X$_2$ or Pt/PtX$_2$, etc, wherein X is halogen. Liquid electrolyte 1 and the solid crystal need to comprise a soluble salt which comprises the same anion as metal/metal salt complex layer 3. The soluble salt comprises LiX, NaX, KX or CaX$_2$, etc, wherein X is halogen. In one embodiment, metal/metal salt complex layer 3 is Ag/AgCl and the soluble salt in liquid electrolyte 1 is KCl.

Insulation case 5 is used for containing liquid electrolyte 1, solid crystal of ionic salt 2 and metal/metal salt complex layer 3. Insulation case 5 may comprise plastic, ceramics or glass, etc. In one embodiment, insulation case 5 is plastic.

Nano-porous junction material 6 is bound to an open end of the insulation case 5 to be in contact with the liquid electrolyte 1 and is a part of the reference electrode of the invention, which is in contact with a measured solution. The pore size of nano-porous junction material 6 is larger than the ion diameter of the ionic salt in the liquid electrolyte 1 but less than the molecular diameter of the water soluble organic compound in the liquid electrolyte and it has three functions. First, the nano-scale pores of the junction material can appropriately increase the resistance of the diffusion of the ions from the liquid electrolyte of the reference electrode into the measured solution. Second, the nano-porous junction material can prevent the organic compound in the electrolytes of the reference electrode because the pore size of the nano-porous junction material is smaller than that of the organic compounds, which sustains the composition of the liquid electrolyte and the electrolyte can always keep the water in the reference electrode. Third, the nano-porous junction material prevents the molecules having a molecular size larger than the pore size of the nano-porous junction structure, such as proteins diffuse through the junction material into the reference electrode to contaminate the liquid electrolyte and results in the shift of the reference electric potential. Therefore, the pore size of nano-porous junction material 6 is larger than the ion diameter of the ionic salt in the liquid electrolyte 1 but less than the molecular diameter of the water soluble organic compound in the liquid electrolyte. In other words, the variety and pore size of nano-porous junction structure 6 may be changed according to the chosen water soluble organic compound in the liquid electrolyte. Nano-porous junction material 6 conforming with the features mentioned above, may comprises zeolite or organic and inorganic complex materials containing zeolite. In one embodiment, the chosen water soluble organic compound is poly(ethylene glycol), the molecular weight thereof is 200 g/mole and the molecular length of the spiral molecule thereof is about 11 Å while nano-porous junction material 6 is zeolite and the pore size thereof is about 4 Å. In other embodiment, a water soluble organic compound having different molecular weights may also be chosen to comply with a nano-porous junction material having other pore sizes.

Although FIG. 1 shows a reference electrode structure of one preferred embodiment, the structure of the invention is not limited thereto. For example, in other embodiments, a semiconductor technology can be applied to manufacture the multilayered reference electrode with the ideas disclosed in this invention. A metal/metal salt complex layer will be formed on the silicon wafer. A gelatinoids or liquid electrolyte composed of the same formula in this invention and a nano-porous junction material is layered on the wafer in sequence. The device is sealed except the nano-porous junction material of the multilayered reference electrode. In addition, nano-porous junction material 6 shown in FIG. 1 also may be embedded in any position of insulation case 5 to comply with different structural designs of the reference electrode and the need for different required features.

EXAMPLE

Example 1

Figure 2:
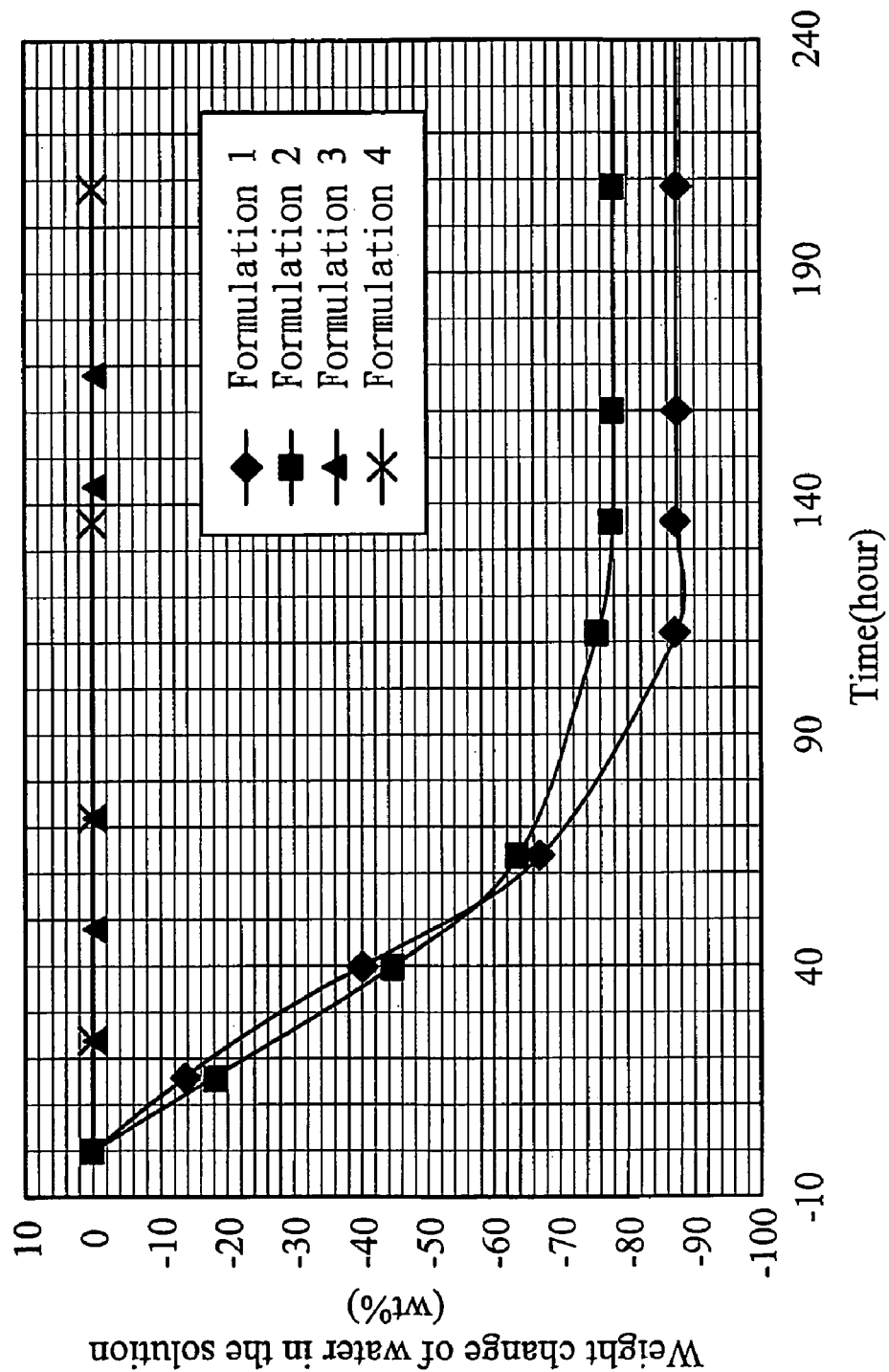
FIG. 2 shows the weight change of the water in a solvent in the formulation of the invention and other formulations at different times under the environment of 35° C., 50 RH %.

The formulations shown in Table 1 were prepared to respectively form electrolytic solutions, and placed in an environment of 35° C., 50 RH %. The test results of the weight change of the water in the different solutions at different times were recorded and are shown in FIG. 2.

TABLE 1

The formulations of different liquid electrolytes

|  | Formulation 1 | Formulation 2 | Formulation 3 (The invention) | Formulation 4 (The invention) |
|---|---|---|---|---|
| LiCl |  | 2.12 g |  |  |
| KCl | 26.09 g |  | 26.09 g | 26.09 g |
| $NH_4NO_3$ |  | 24.01 g |  |  |
| Agar |  | 3 g |  |  |
| $H_2O$ | 89.07 g | 82.10 g | 11.27 g | 1.97 g |
| PEG 200 |  |  | 62.64 g |  |
| PPG 450 |  |  |  | 71.94 g |

*The average molecular weight of PEG 200 is 200; the average molecular weight of PPG 450 is 450.

In Table 1, the solvents of formulation 1 and 2 were water, and the solvents of formulation 3 and 4 were the mixture solution of PEG 200 and water and the mixture solution of PPG 450 and water, respectively. Except for water being a volatile ingredient in the formulations, all other ingredients were non-volatile at normal atmosphere and 35° C., thus the weight changes of formulations were the weight changes of water. FIG. 2 shows the weight changes of water in different formulations.

Formulation 1 was a 3.5 M KCl solution. In the environment of 35° C., 50 RH % formulation 1 lost water quickly and finally only 10 wt % of water remained. Formulation 2 was the formulation of the liquid electrolyte suggested by U.S. Pat. No. 5,334,305. Although formulation 2 maintained much water compared with the 3.5 M KCl solution in a dry environment, formulation 2 still lost water close to 80 wt %. Although the water content of formulation 3 and 4 were only 15% and 13% of the total weight of the solvent thereof, respectively, the weights of formulation 3 and 4 did not obviously change in a dry environment of 35° C., 50 RH % for 280 hours. This result showed that PEG 200 and PPG 450 are strong hydrophilic and can hold water in the electrolytic solution. Accordingly, PEG 200 and PPG 450 prevented the reference electrode from malfunction, which results from the liquid electrolyte vaporizing in low humid

Example 2

Four plastic tubes having the same length and the same caliber were used. Zeolite was embedded in one end of each tube, and different electrolyte formulations were poured in to each tube, respectively from the other end of each tube. Then, the other end of each tube was sealed and the sealed position was ensured to prevent the electrolyte formulations from flowing out from the sealed position. The diameter and cross-section area of the exposed part of the zeolite embedded of the four tubes were the same. The pore sizes of zeolite embedded in the four tubes were listed as in Table 2. Then, the four tubes were soaked into the deionized water, respectively, for 24 hours. After that, the deionized water was titrated with AgNO3 solution to determine the amount of KCl flowing out from the nano-porous junction material of the plastic tube.

TABLE 2

The influence of pore size of zeolite and the formulation of electrolyte on the leaching rate of KCl in the reference electrode

|  | Sample 1 | Sample 2 | Sample 3 | Sample 4 |
|---|---|---|---|---|
| Pore size of zeolite | 3 Å | 4 Å | 5 Å | 4 Å |
| Formulation of liquid electrolyte | Formulation 3 | Formulation 3 | Formulation 3 | Formulation 1 |
| leaching rate of KCl (mg/24 hr) | 1.264 | 2.03 | 3.97 | 4.59 |

In Table 2, the liquid electrolytes of samples 1-3 are formulation 3 shown in Table 1, however the pore sizes of zeolite of samples 1-3 were different. Accordingly, the three samples show the influence of pore size of zeolite on the leaching rate of KCl in the reference electrode. The results in Table 2 show that the larger the pore size of zeolite is, the higher the leaching rate of KCl.

Furthermore, the pore sizes of zeolite in samples 2 and 4 were 4 Å, but the formulation of the liquid electrolyte of sample 2 and the formulation of the liquid electrolyte of sample 4 were different. The formulation of the liquid electrolyte of sample 2 is the formulation of the invention and the formulation of the liquid electrolyte of sample 4 is the KCl solution used in traditional reference electrode. The two samples show the influence of the formulation of electrolyte on the leaching rate of KCl in the reference electrode. The results in Table 2 show that the leaching rate of KCl of the formulation of the invention is much lower than the traditional liquid electrolyte.

Example 3

An Ag/AgCl reference electrode having different junction material from the traditional reference electrode was produced. The structure of the reference electrode was the same as that shown in FIG. 1. The processing method is described in the following.

Electroplating: One end of an Ag wire (diameter 0.5 mm, length 1 mm, purity 99.95%) was connected with an electric wire as an leading wire. Then, the Ag wire was soaked in 0.3 M HCl and electroplated with 0.8V voltage for 10 minutes to form AgCl on the surface of the Ag wire.

The formulation of the liquid electrolyte was: 26.09 g of KCl, 73.1 g of PEG 200, and 13.30 g of water.

Zeolite (pore size 4 Å) was embedded in one end of a plastic tube (inner diameter 3 mm, length 15 mm) as a junction material of the reference electrode. The gap between the junction material and the plastic tube was sealed up by epoxy. Then, liquid electrolyte was poured and Ag/AgCl wire was disposed into the plastic tube from the other end. After that, the other end of the plastic tube was sealed up by epoxy and the reference electrode was completed. Furthermore, a traditional Ag/AgCl glass reference electrode was used as a counterpart, for testing the features of the reference electrode. The traditional Ag/AgCl glass reference electrode used porous glass as the junction material and a saturated solution of KCl as the liquid electrolyte.

The reference electrode having zeolite as the junction material and the traditional Ag/AgCl glass reference electrode mentioned above were soaked in the buffer (pH 4). Then, the electric potential changes of the two reference electrodes during a long period of time were measured by a standard hydrogen electrode which was used as a reference electrode. The results of the measurement were showed in FIG. 3.

Figure 3:
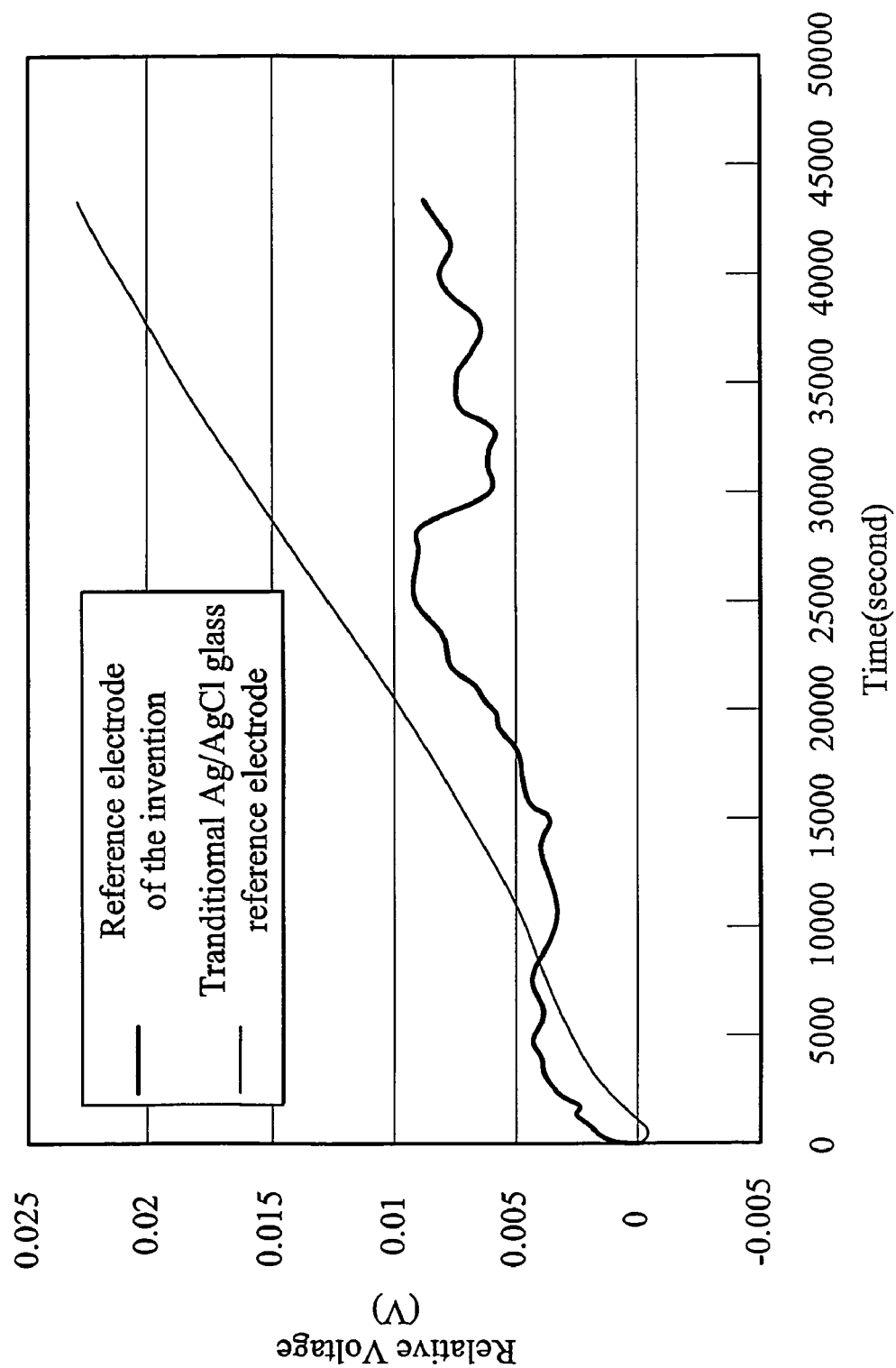
FIG. 3 shows stability of electric potential of the reference electrode having zeolite as a junction material of one embodiment of the invention and the traditional Ag/AgCl glass reference electrode.

FIG. 3 shows that the reference electrode having zeolite (pore size 4 Å) as the junction material had better stability of electric potential than the traditional Ag/AgCl glass reference electrode. In the buffer (pH 4) and continuously tested for 12 hours, the electric potential change of the reference electrode having zeolite (pore size 4 Å) as the junction material was less than 8 mV but the electric potential change of the traditional Ag/AgCl glass reference electrode was about 22 mV. Therefore, the reference electrode of the embodiment of the invention had better stability of electric potential during a long period of time. In addition, when the reference electrode of the invention was not being used, no storage in a saturated solution of KCl was required, and the size thereof was much less than the traditional Ag/AgCl glass reference electrode.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A reference electrode, comprising:
   a liquid electrolyte containing water, a water soluble organic compound with molecular size and boiling point both greater than water, and an ionic salt, wherein the water soluble organic compound is poly(polypropylene glycol) with the average molecular weight of 450;
   a solid crystal of the ionic salt in the liquid electrolyte;
   a metal/metal salt complex layer in contact with the liquid electrolyte;
   a leading wire connected to the metal/metal salt complex layer;
   an insulation case for containing the liquid electrolyte; and
   a nano-porous junction material bound to an open end of the insulation case for contacting the liquid electrolyte, wherein the nano-porous junction material has a pore size of about 4 Å and the pore size is greater than the diameter of the cation of the ionic salt but smaller than the average molecular length of the water soluble organic compound.

2. The reference electrode as claimed in claim 1, wherein the liquid electrolyte contains about 5-50 wt % water.

3. The reference electrode as claimed in claim 2, wherein the liquid electrolyte contains less than about 30 wt % water.

4. The reference electrode as claimed in claim 1, wherein the metal/metal salt complex layer comprises Ag/AgX, Hg/Hg$_2$X$_2$ or Pt/PtX$_2$, where X is halogen.

5. The reference electrode as claimed in claim 1, wherein the ionic salt in the electrolyte has the same anion as does the metal/metal salt complex layer.

6. The reference electrode as claimed in claim 5, wherein the ionic salt comprises LiX, NaX, KX or CaX$_2$, where X is halogen.

7. The reference electrode as claimed in claim 1, wherein the insulation case comprises plastic, ceramics or glass.

8. The reference electrode as claimed in claim 1, wherein the nano-porous junction material comprises zeolite or an organic and inorganic hybrid material containing zeolite.

* * * * *